United States Patent [19]
Christensson

[11] Patent Number: 5,624,281
[45] Date of Patent: Apr. 29, 1997

[54] CLASP STRUCTURE FOR BIOMEDICAL ELECTRODES

[76] Inventor: Eddy K. G. Christensson, 4016 Inglewood Ave. S., Edina, Minn. 55416

[21] Appl. No.: 355,954

[22] Filed: Dec. 14, 1994

[51] Int. Cl.[6] ............................. H01R 4/48; H01R 13/15
[52] U.S. Cl. ........................ 439/729; 439/909; 439/261; 439/859
[58] Field of Search ........................... 439/729, 859, 439/854, 259, 261, 909, 465, 456

[56] References Cited

U.S. PATENT DOCUMENTS

| | | | |
|---|---|---|---|
| D. 251,387 | 3/1979 | Ramsay et al. | D24/29 |
| 2,465,722 | 3/1949 | Hamilton | 173/273 |
| 3,090,029 | 5/1963 | Stroebel | 339/255 |
| 3,456,181 | 7/1969 | Godshalk | 320/25 |
| 3,543,760 | 12/1970 | Bolduc | 128/416 |
| 3,624,590 | 11/1971 | Bolduc | 339/75 R |
| 3,642,008 | 2/1972 | Bolduc | 128/416 |
| 3,671,924 | 6/1972 | Nagano | 339/95 D |
| 3,694,791 | 9/1972 | Urban | 339/75 T |
| 3,699,968 | 10/1972 | Bolduc | 128/303.13 |
| 3,810,075 | 5/1974 | Turner | 439/465 |
| 3,817,253 | 6/1974 | Gonser | 128/418 |
| 3,824,529 | 7/1974 | Dorrell | 339/99 |
| 3,842,394 | 10/1974 | Bolduc | 339/75 R |
| 3,868,165 | 2/1975 | Gonser | 339/97 R |
| 3,895,635 | 7/1975 | Justus et al. | 439/909 |
| 3,914,007 | 10/1975 | Seidler | 339/255 P |
| 4,026,278 | 5/1977 | Ricketts et al. | 439/859 |
| 4,040,697 | 8/1977 | Ramsay et al. | 339/61 R |
| 4,061,408 | 12/1977 | Bast et al. | 439/729 |
| 4,151,462 | 4/1979 | Texler | 324/72.5 |
| 4,365,634 | 12/1982 | Bare et al. | 128/640 |
| 4,449,772 | 5/1984 | Johnson, III | 339/29 B |
| 4,453,791 | 6/1984 | Ledbetter | 339/29 B |
| 4,555,155 | 11/1985 | Drake | 339/61 R |
| 4,640,563 | 2/1987 | Le Blanc | 339/32 M |
| 4,647,131 | 3/1987 | Van Woensel | 339/74 R |
| 4,685,886 | 8/1987 | Denlinger et al. | 439/55 |
| 4,702,256 | 10/1987 | Robinson et al. | 128/639 |
| 4,761,143 | 8/1988 | Owens et al. | 439/372 |
| 4,795,857 | 1/1989 | McInnis | 439/731 |
| 4,797,125 | 1/1989 | Malana | 439/729 |
| 5,295,872 | 3/1994 | Christensson | 439/822 |
| 5,407,368 | 4/1995 | Strand et al. | 439/729 |

FOREIGN PATENT DOCUMENTS 1073056  1/1960  Germany ..................... 21/22

OTHER PUBLICATIONS

Commercial product Sheets: NDM Corporation, Dayton, Ohio; Fastener System Product Numbers D3–6000 to 7202 from 1991 Catalog.
Commercial Product: EKG Clip marketed by Hirschman of America, Riverdale, New Jersey.
Commercial Product: "Astro–Trace" Clip marketed by Le Blanc Corporation, Augusta, Georgia.
Commercial Product: EKG Clip marketed by Trono Med, Inc., Irvine, California.
Commercial Product: EKG Clip marketed by 3M Company, St. Paul, Minnesota.

*Primary Examiner*—P. Austin Bradley
*Assistant Examiner*—Yong Kim
*Attorney, Agent, or Firm*—James V. Harmon

[57] ABSTRACT

A clasp for a biomedical electrode includes opposed cooperating jaw members. The jaw members can be end portions of a U-shaped leaf spring. A lever is pivotally mounted for engagement with the jaws for forcing the jaws together to grip an electrode placed between them. An opening is provided within the clasp for receiving the stud of a different style electrode and a retaining tab or finger is provided for engagement with the stud to shift the stud to a locked position in the opening when the lever is pivoted toward its operative position.

22 Claims, 5 Drawing Sheets

CLASP STRUCTURE FOR BIOMEDICAL ELECTRODES

FIELD OF THE INVENTION

This invention relates to improved electrical clasp structures for transferring biomedical electrical signals.

BACKGROUND OF THE INVENTION

This invention is concerned with a biomedical clasp structure and especially, although not exclusively, with one capable of universal use, i.e., use with both kinds of external skin contacting electrode sensors (tab and snap types) now in use for substantially interference-free transfer of body or cardiovascular (CV) signals to electrocardiographic equipment for making ECG measurements, producing displays or for providing electrical stimulation to the body of a patient.

Disposable external electrode sensors for ECG readings are placed in contact with a patient at selected locations about the torso and limbs. These sensors are held adhesively to the skin surface and include a conductive gel or membrane that chemically reduces the resistance presented by the skin and thereby promotes the transmission of CV electrical impulses from the body of the patient via the electrodes to the associated detecting means. Two types of external disposable electrode sensors are in general use. The selection of either type is dependent on measuring conditions. One type used with the patient in a prone position for short-term measurements is a thin sheet form of electrode with an exposed planar tab for transferring sensed electrical signals. An alligator clip with jagged-edge gripping means has typically been used on an exposed planar contact tab. Another type of electrode generally used for longer-term measurements, for example, when the patient is exercising and/or being monitored for prolonged time periods, has a central metallic contact such as a male lug or nut.

As seen in FIG. 3 of U.S. Pat. No. 4,640,563 to LeBlanc, a prior art alligator clip includes jagged edge jaws at its working end and a handle for opening the jaws. As a part of the prior art connector structure, a lead wire is electrically connected by solder to one arm of the alligator clip. At the opposite longitudinal end of the lead wire, a female receptacle is provided for receiving a male member for electrical connection to the measuring equipment.

However, such an alligator clip has certain disadvantages and, in particular, cannot provide desired electrical contact and stability with a snap style contact stud. Because of the differing types of sensors and connectors, delays have occurred due to inferior and/or loose connections resulting in much frustration for the EKG operator since such connections can ruin the recording and prevent the machine from properly performing the test. Thus, it would require repeat tests and manual resecuring of prior art connections to the patient.

Because of the exposed lead wire, and other aspects of prior connectors, they could not be sterilized for use in a sterile environment, had short-term life expectancy in non-sterile environments and, in general, did not provide optimum recovery of the low-energy-level patient signals available.

The present invention overcomes these problems and disadvantages by providing a single type of electrical clasp structure for obtaining accurate ECG measurements from the planar tab type electrode structures used for sensing patient signals, and allows for easy and rapid connection of a male connector leading to an electrical measuring and indicating device.

U.S. Pat. No. 4,061,408 describes a connector having an L-shaped lever arm. In the development of the present invention, it was found that such a lever is often awkward to use and is therefore not fully acceptable from a human engineering standpoint. In developing the present invention, it was noticed that the direction of lever rotation in U.S. Pat. No. 4,061,408 opposes the natural motion of the clasp itself as it is attached and later disconnected from the electrode. In addition, the patented clasp is only suited for the tab type of planar electrode. One important objective of the present invention is to overcome these deficiencies.

In contrast to the prior art, the present invention is well adapted for use with both the planar tab-type external electrode and the snap-type electrode in any type of patient monitoring or stimulation environment. It also provides a streamlined configuration. The structure can also be usefully employed, as well, in any so-called tab TENS (muscle stimulating electrode) environment and with other stimulation electrodes.

SUMMARY OF THE INVENTION

In order to establish electrical contact with a biomedical electrode, a preferred embodiment of the invention provides a clasp structure with a pair of jaws and a lever for closing the jaws when the lever is moved toward the end of the clasp where the jaws are located. Optionally, the clasp has a stud-receiving opening in which the stud of an electrode is held when the lever is moved to an operative position.

The invention will be better understood by reference to the figures and detailed description which illustrate by way of example a few of the various forms of the invention within the scope of the claims.

DETAILED DESCRIPTION OF THE INVENTION

Figure 1:
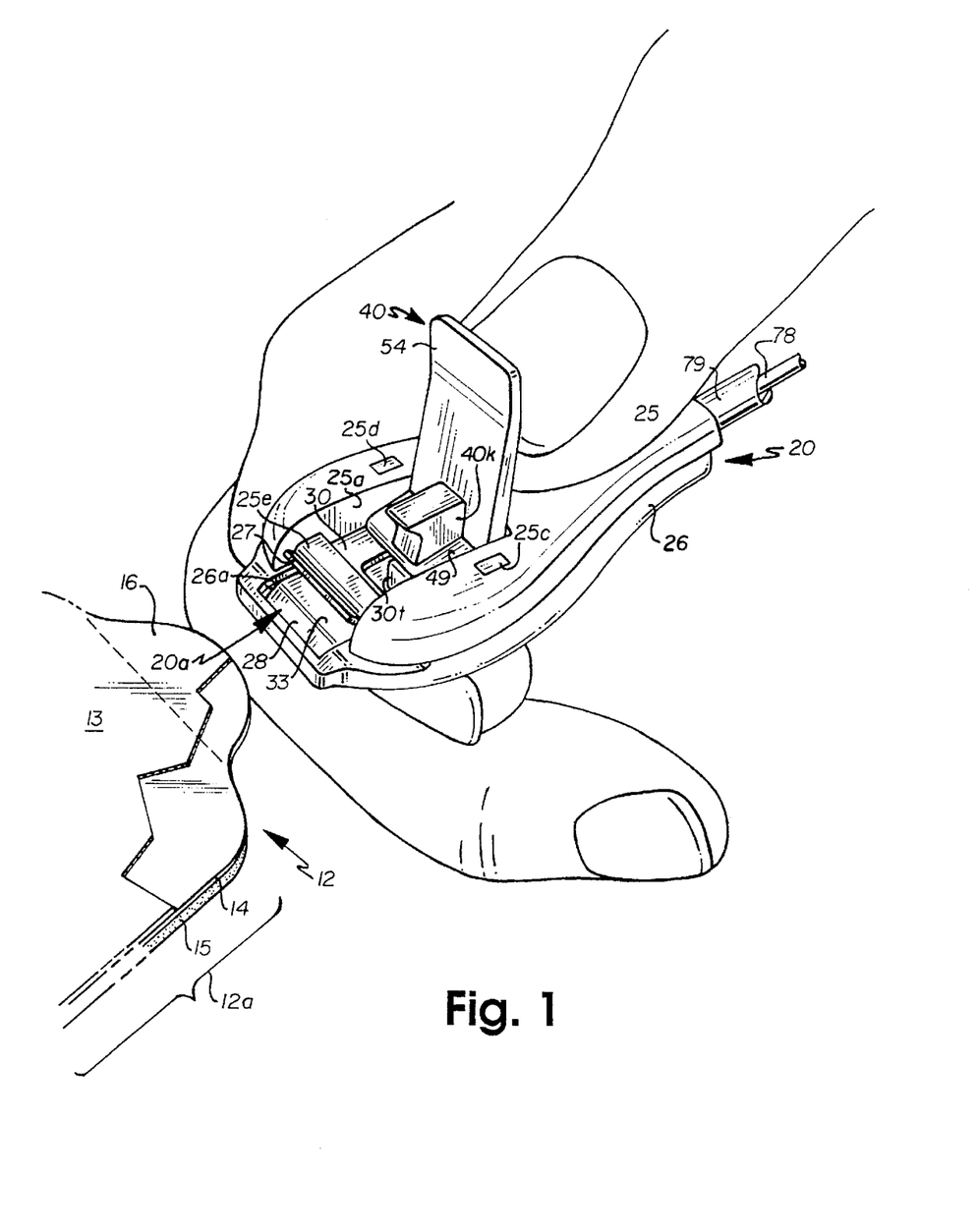
FIG. 1 is a perspective view of the new clasp just before the jaws are closed on a planar tab-type of external electrode which has been in general use.

In FIG. 1 a flexible, planar tab-type biomedical electrode sensor 12 is shown by way of example as a thin sheet of plastic 13 with a plated electrically conductive silver layer 14. The conductive layer 14 has a signal-sensing portion 12a and a signal transfer tab 16. On the lower surface of silver layer 14 is an electrically conductive hydrogel layer 15 which bonds to the skin of the patient and forms electrical contact therewith. The laterally extending signal transfer tab 16 is accessible for transfer of electrical signals sensed by the gel portion 15 which is in contact with the skin of the patient.

In the side and top views of the clasp connector of the present invention (FIGS. 4 and 5), a typical planar electrode 12 is shown with the signal transfer tab portion 16 in locking engagement with the present clasp structure indicated generally at 20a.

Figure 3:
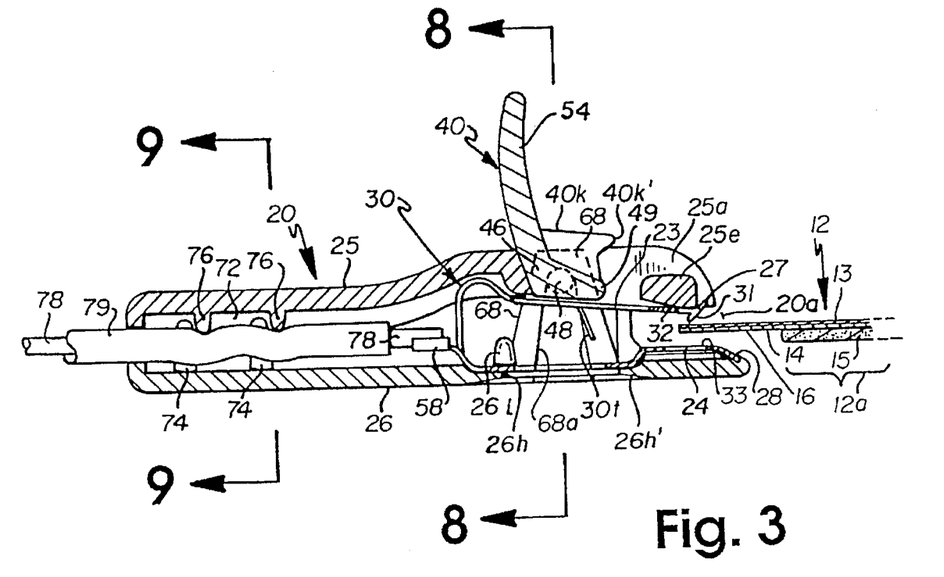
FIG. 3 is a vertical, longitudinal sectional view of a preferred embodiment of the present invention (substantially enlarged) with the jaws positioned in the non-operative open mode.

In FIGS. 1 and 3, an enlarged view of the clasp 20 is depicted in the non-operative mode, i.e., the clasp jaw opening 20a is not in clamping electrical contact with electrode 12. The clasp body 20 has a front or jaw end at the right and a rear end at the left as shown in the figures. Clasp 20 includes a flat leaf spring 30 with a pair of elongated arms 23 and 24 which serve as jaws, with aligned clasp surfaces presenting integral electrical contact surfaces 32, 33 confronting each other. The contact surfaces 32, 33 are normally biased by the elasticity of spring 30 in an open spaced apart relationship as shown.

When the clip arms or jaws 23, 24 are biased in a spaced-apart posture, they will admit the insertion of the tab 16 of a biomedical electrode like 12 of FIG. 1. If desired, the inner electrical contact surfaces 32, 33 can be serrated for good electrical contact and mechanical gripping of inserted electrodes. Most preferably, the upper contact surface 32 is provided with a pair of laterally spaced, downwardly and inwardly projecting teeth or barbs 31 (FIGS. 3, 10 and 12–14) formed by making a V-shaped cut in the spring 30 for more reliably gripping the signal transfer tab 16.

The inner contact surfaces 32, 33 of the jaw portions of the clip arms 23, 24 are configured to grasp the signal transfer tab 16. This is accomplished by forcing the contact surfaces 32, 33 toward one another to provide a firm grip on the tab 16 of electrode 12.

Spring 30 is metallic for conductive purposes, preferably being of plated, annealed spring steel (1050° grade, heat treated to Rockwell 45 hardness) or stainless steel and is completely sterilizable upon disconnection from the electrode 12 between uses. The spring 30 has a gauge of 0.012"±0.00075" and is plated first with copper and then with laboratory grade nickel. As shown, the contact surfaces 32, 33 are well spaced apart until ready to clasp the electrode 12.

Affixed above the intermediate portion of upper clip arm 23 is a thumb-length jaw operating lever 40 which rotates forwardly on laterally extending aligned pivots 48 between a lever-up inoperative position (FIG. 3) and a lever-down operating position (FIG. 4) in line with the clasp body. In the latter position, the electrode 12 is gripped tightly between the contact surfaces 32, 33 of clip arms 23, 24. It should be noted that during the jaw closing operation, the free end 54 of lever 40 swings forwardly toward the jaw opening 20a. This permits it to be easily operated with the finger or thumb, tending to move the open clasp 20 toward engagement with the electrode 12 rather than away from it. This gives the clasp 20 superior closing characteristics from a human engineering standpoint.

Figure 4:
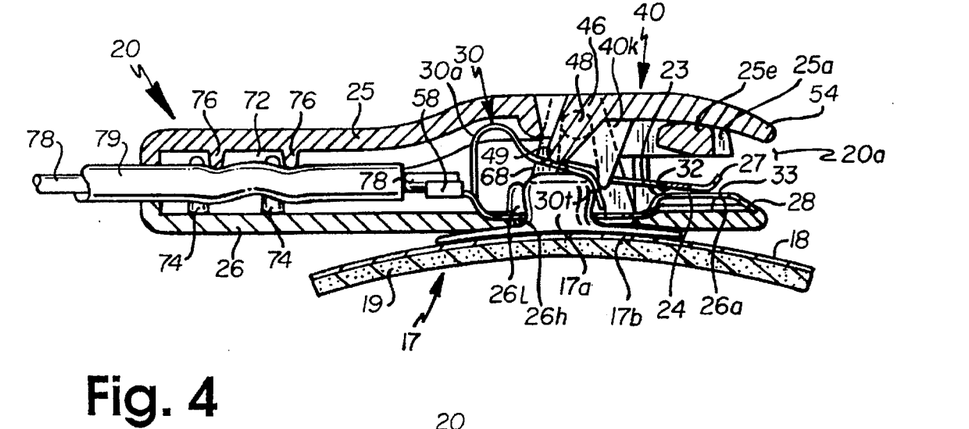
FIG. 4 is a vertical, longitudinal sectional view of the embodiment of FIG. 3, with the clasp in the operative mode, i.e., closed.
Figure 5:
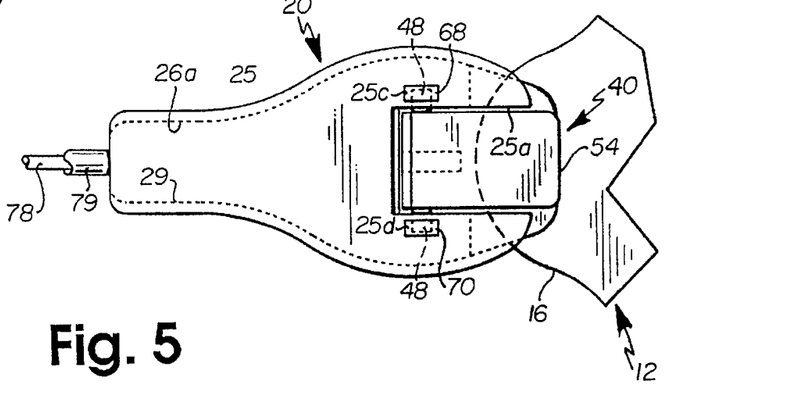
FIG. 5 is a top plan view of the clasp structure of FIG. 4 when in the operative mode.

The lower end 46 of lever 40 has a protrusion or cam 49 which engages the top of spring 30 (FIGS. 4 and 5). In the lever-up inoperative position of FIGS. 1 and 3, the protrusion 49 allows the contact surfaces 32, 33 of clip arms 23, 24 to be spaced apart. In the in-line or operating lever position, the cam 49 biases the upper portion 36 downwardly, clamping the contact surfaces 32, 33 of clip arms 23, 24 on the tab 16 as in FIG. 4.

When the clasp 20 is to be employed with electrodes already in place on a patient's body, and while the contact surfaces 32, 33 are still in the open posture, they are slipped over the electrode tab 16 and then closed with a finger or thumb by rotating lever 40 forwardly, i.e., toward free ends 27, 28 of the jaws and the electrode 12 itself, causing the protrusion 49 to compress the middle portion of spring 30 so as to move the upper arm 23 downwardly into locking closure on the electrode 12 (see FIG. 4). The electrode 12 is then secured against normal jostling or cable flexure, until the clasp 20 is purposefully released by prying lever 41 upwardly and rearwardly.

Figure 6:
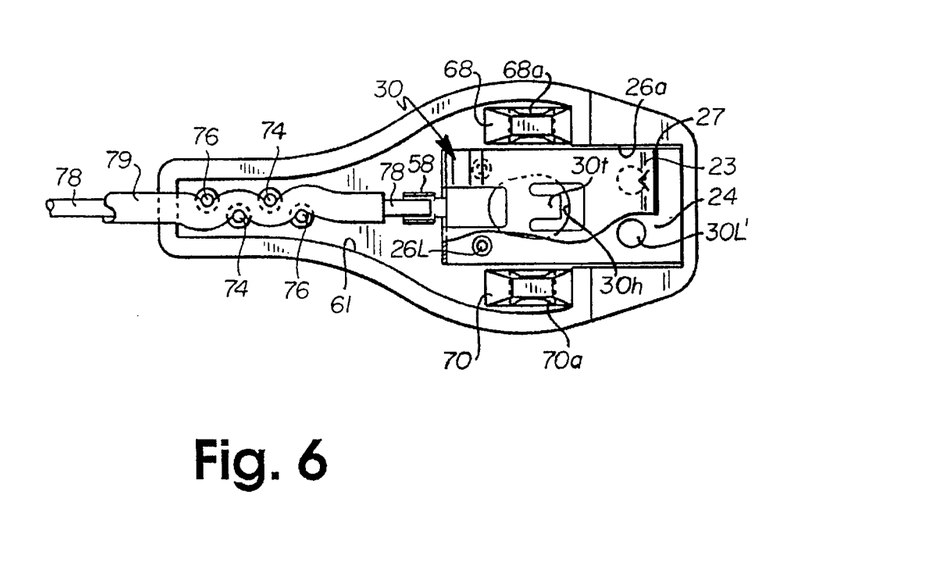
FIG. 6 is a plan view of the bottom portion of the clasp with the spring and lead wire installed.

In a preferred embodiment (FIG. 3), the spring 30 is generally U-shaped and has a closed end 30a as seen at the left in FIGS. 3 and 4. The clasp 20 includes an upper body portion 25 and a lower body portion 26. During assembly, the spring 30 is dropped onto the clasp lower body portion 26 and after assembly its free ends 27, 28 rest snugly against adjacent clasp inner pocket 26a (FIGS. 1 and 6). The closed portion, i.e., the left end 30a of the spring 30 is also provided with a centrally-positioned, rearwardly extending, rigid, trough-shaped, electrically conductive lug 58. An electrical lead 78 has its inner end contacting the surface of the lug 58 and is preferably soldered to it.

Figures 7, 7A, 8:
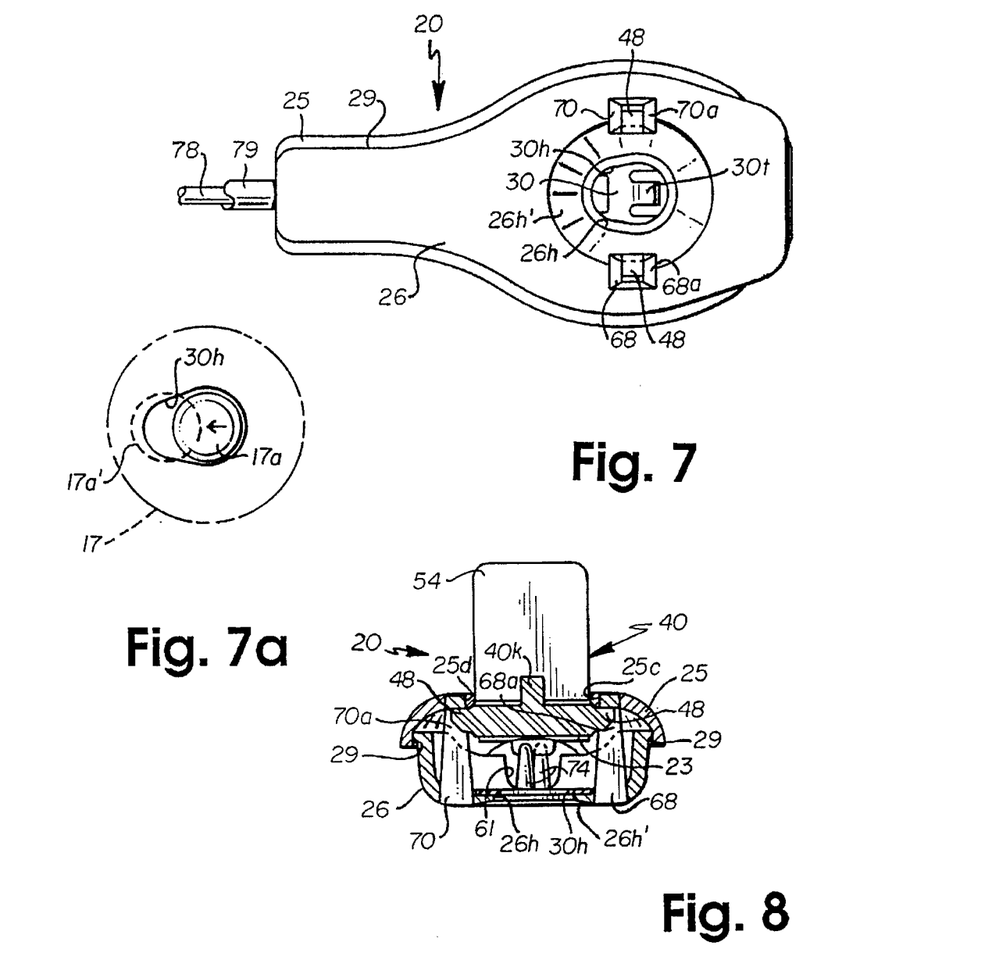
FIG. 7 is a bottom view of the invention.
FIG. 7A is a bottom view of an opening in the bottom of the clasp as it appears when a stud of the snap-type electrode is inserted therein.
FIG. 8 is a vertical cross-sectional view taken on line 8—8 of FIG. 3.

The upper and lower portions 25 and 26 of the clasp 20 are of a molded material, preferably plastic resin which has electrical insulating properties, typically of nylon or polycarbonate plastic which is completely sterilizable. The upper portion 25 has a forwardly facing, upwardly opening, central cavity 25a to receive the lever 40 (FIG. 5). The lower portion 26 has an upwardly facing recess 26a aligned beneath it to receive the spring 30. On either side of the spring 30 are upwardly extending lever supporting posts 68, 70 which have laterally aligned central openings 68a, 70a to receive the pivots 48 of the lever 40 (FIG. 8). During assembly, the lever 40 is mounted by forcing the upper ends of the supporting posts 68, 70 apart slightly and then allowing them to snap back toward one another to enclose the pivots 48 of lever 40. The upper portion 25 of the clasp 20 is then forced downwardly onto the lower portion 26, causing the tops of the posts 68, 70 to enter openings 25c and 25d (FIG. 5) as a peripheral snap connection 29 (FIGS. 5, 8 and 9) locks the upper and lower portions 25, 26 together. The posts 68, 70 are then held permanently in the openings 25c, 25d which act as retaining means so that they can no longer be spread apart. The lever 40 will, therefore, resist being dislodged by a force many times the force required to separate snap connection 29. When the lever 40 is pivoted forwardly, the posts 68, 70 hold it securely in place. It is not the snap connection 29 which holds it since the entire load exerted by the lever 40 is carried by the posts 68, 70. This feature of the invention provided by the advantage of having the load carried by posts 68, 70 makes it possible to assemble the invention without the necessity of welds which reduces manufacturing costs. The posts 68, 70 will, in fact, hold a force applied to the lever 40 that is twenty times that which is needed to open the clasp 20 at the snap connection 29.

Figure 9:
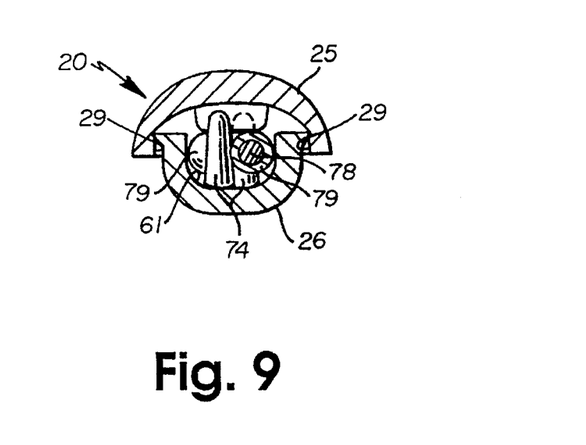
FIG. 9 is a vertical cross-sectional view taken on line 9—9 of FIG. 3.
Figure 10:
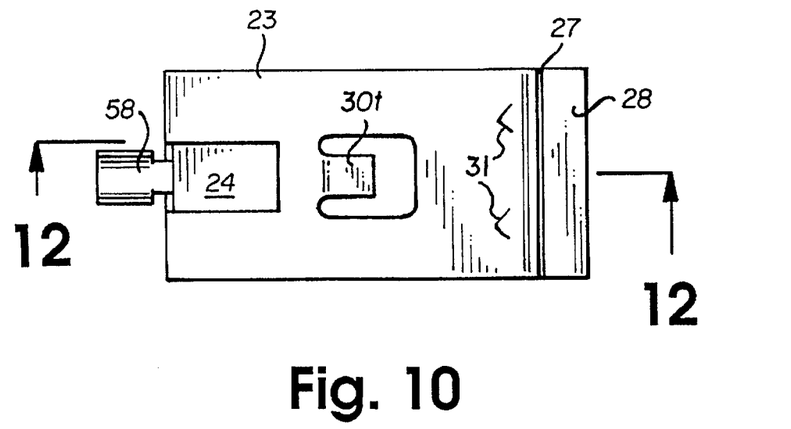
FIG. 10 is a plan view of the spring.
Figure 11:
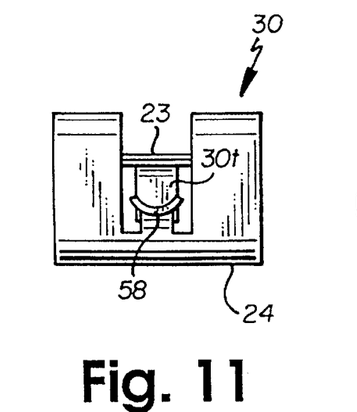
FIG. 11 is a left-end view of the spring.
Figure 12:
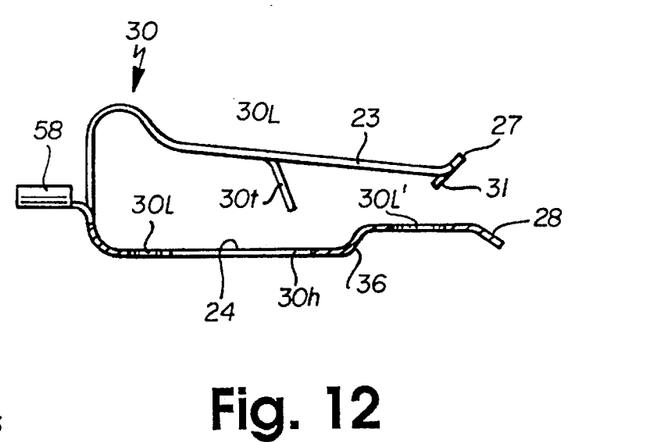
FIG. 12 is a vertical cross-sectional view of the spring taken on line 12—12 of FIG. 10.
Figure 13:
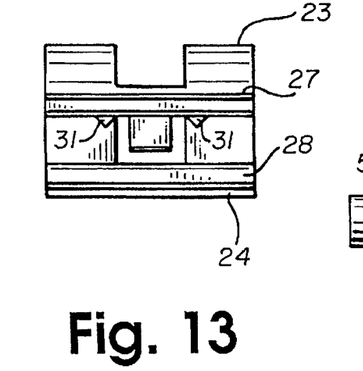
FIG. 13 is a right-end elevational view of the spring.
Figure 14:
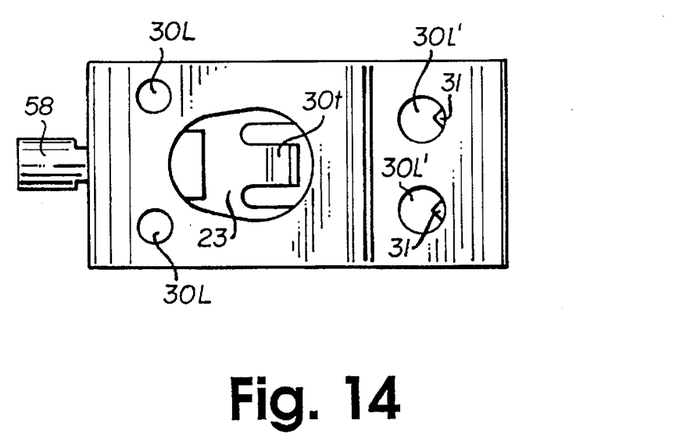
FIG. 14 is a bottom view of the spring.

An insulating sleeve 79 surrounds an insulated electrically conductive cable or lead 78 which is also connected at its distal end to a meter or other measuring means or source of current for stimulation (not shown). The lead 78, 79 is shown passing through a central opening 61 in the clasp 20 (FIGS. 6, 8 and 9). The vertical sectional views of FIGS. 8 and 9 show the clasp body 20 provided with a discrete U-shaped internal channel 61 therethrough, in which the inner terminal length of lead 78 rests. The lead 78, 79 is held in a serpentine passage between staggered pins including two upper retaining pins 76 and two lower retaining pins 74. The pins 74, 76 act as a maze which serves as a strain relief function and are fabricated as a part of the upper and lower portions 25, 26 of the clasp 20.

Figure 2:
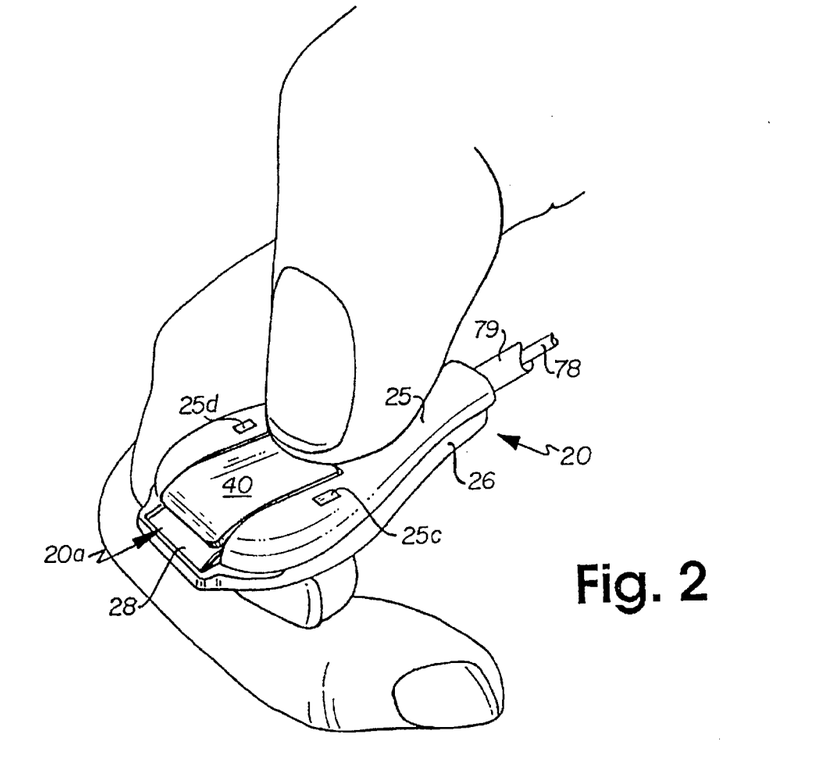
FIG. 2 is a view similar to FIG. 1 with the clasp jaws in the closed position.

The operative mode of the clasp 20 is depicted in FIGS. 2 and 4, in which a planar signal transfer tab 16 (FIG. 1) is firmly gripped between the contact surfaces 32, 33 of clip arms 23, 24. Lever 40 has been rotated forwardly to be in line with the longitudinal dimension of clasp 20, causing cam 49 to rotate clockwise as seen in FIG. 4 and bias downwardly the upper arm 36 of spring 30 to hold the jaws in clamping position.

The free length of lead 78, 79 is retained in operative contact by the crimping of retaining pins 74, 76 in the channel 61 and conductor 78 is soldered to lug 58 (FIG. 3).

To assemble the clasp 20, the conductor 78 is first soldered to lug 58. The lead 78, 79 is then threaded through channel 61 between the pins 74, 76. Lever 40 is then snapped into place on the posts 68, 70. The upper and lower outer insulator casing portions 25, 26 are then snapped together at 29 and the assembled clasp 20 with its coupled cable 78, 79 is ready for use.

In FIG. 5 is shown a top plan view of the clasp 20 with the lever 40 in the operating mode. In this mode the lever 40 is thrown forwardly into the upwardly opening cavity 25a which receives the free end 54 of the lever 40, providing a clasp that is free of projections and has a smoothly contoured surface. Extending laterally across the open end of the cavity 25a is a lever support bar 25e.

The feature of the invention used for holding a snap-type electrode will now be described in connection with FIGS. 4 and 7.

Near the center of the bottom portion 26 of the clasp 20 is an oblong opening 26h which is slightly larger at its forward end as shown in FIG. 7. Around the opening 26h is an upwardly and centrally tapered surface 26h'. Aligned above it is a similarly shaped opening 30h in the lower arm 24 of the spring 30. The spring 30 is also provided with two pairs of openings 30l and 30L' in the lower arm 24. The openings 30l are placed over aligned locating pins that project upwardly from the lower surface of the lower portion 26 of the clasp 20 for holding the spring 30 in place. The openings 30L' receive the barbs 31 when the jaws 20a are closed. The forward portion of the opening 26h and the forward portion of the opening 30h of the spring 30 are large enough to accommodate the stud 17a of a snap-type electrode 18 shown in FIG. 4. When the stud 17a is introduced into the forward enlarged end of the opening 30h in the spring 30 through opening 26h, it can do so because the opening is large enough at its forward end to accommodate the stud 17a. However, when the lever 40 is thrown forwardly and downwardly to the operating position, a keel 40k provided as an integral part of the lever 40 exerts a rearward force on a downwardly projecting tab or finger 30T which extends downwardly from the upper spring arm 23, causing tab 30T to be deflected rearwardly so as to shift the lug or stud 17a of the snap-type electrode 18 rearwardly in the oblong opening 30h, thereby locking it in place. The stud 17a is shown shifted rearwardly to its locked position at 17a' in the opening 30h in FIG. 7A. It will be noticed that the upper end of the stud 17a is slightly enlarged. This enlargement will prevent the stud 17a from being withdrawn once the locking tab 30T is deflected rearwardly by the downward pressure applied by the keel 40k (FIG. 4). The tab or finger 30T also acts as a means for establishing electrical contact with the stud 17a.

Because the clasp of the present invention will handle both a tab-type electrode (FIG. 1) or a snap-type electrode as shown in FIG. 4, the clasp of the present invention can be considered a universal clasp, i.e., it will handle both types of biomedical electrodes now in use. It is therefore is much more convenient and provides an additional safety factor since it is ready for use with either type of electrode now employed in hospitals and clinics.

The present invention is also adapted for use and reuse in a sterile environment. The clasp 20 can be repeatedly sterilized in a steam autoclave. The capability of sterilizing the entire clasp structure in a steam autoclave is an advantage which was not available with certain prior art structures because of the lead wire construction.

In practice, the spring 30 can be fabricated from low carbon, cold-rolled steel having a nominal thickness of about 0.012". The entire structure is coated by medical-grade plating with nickel, so that no portion of the clasp is subject to rusting. Preferably an initial copper flash coating is applied, followed by a coating of laboratory grade nickel. In the alternative, stainless steel is used with no plating. A typical embodiment has an overall length of about 3.5 cm and a height of about 0.7 cm. The length of lever 40 is about 1.2 cm.

The forward movement of the lever 40 toward the jaw-end of the clasp 20 at the right in FIGS. 1–4 provides a surprising improvement over the prior art since the movement of the finger or thumb in closing the jaws automatically pushes the clasp 20 in the correct direction to move the jaws onto the tab 16 or, in the case of a snap, to move the lug 17 toward the back of the opening 26h. It was discovered that this provides a surprising advantage from a human engineering standpoint. It should also be noticed that the reverse movement of the lever 40 has the same effect with the clasp 20 is being disconnected from the electrode. That is to say, the lever action helps to move the clasp 20 away from the electrode 12. This is particularly important since the opening and closing of the clasp 20 is carried out with one hand as one hand holds the clasp with the lead wire 78, 79 extending away from the clasp 20 in a line parallel with a person's arm. Since everything is accomplished with one hand, human engineering advantages of the invention are particularly significant and beneficial.

Many variations of the present invention within the scope of the appended claims will be apparent to those skilled in the art once the principles described herein are understood.

What is claimed is:

1. A clasp structure capable of being releasably secured to a planar tab-type contact of a biomedical monitoring or stimulating electrode for carrying current to or from a body of a patient comprising, a) a clasp body having an upper body portion and a lower body portion, b) a pair of opposed jaw members at a front end of the clasp body with a jaw opening therebetween, c) at least one jaw member having an electrical contact at a free end thereof and the jaw members being aligned in opposed relationship confronting each other at the front end of the clasp, d) a resilient spring means operatively supported between the upper and lower body potions and associated with the jaw members for biasing the jaw members toward an open position wherein the jaw members are spaced apart from one another, e) a lever means movably mounted as a part of the clasp and operatively associated with the jaw members, said lever having an exposed portion to which pressure can be applied with a finger or a thumb toward said front end of the clasp for closing the clasp, f) said lever is movably supported on the clasp body and has a jaw-actuating protrusion that extends toward the jaws, g) said jaw-actuating protrusion closes the jaws when the lever is moved toward the front end of the clasp body where the jaw members are located so that a closing direction of the lever coincides with a direction of movement of the clasp as the clasp is being attached to the electrode to facilitate one-handed operation, and h) means for electrically connecting at least one of the jaw members to an electrical lead wire.

2. The clasp structure of claim 1 with a serpentine opening for receiving and retaining the lead wire in-place within the clasp.

3. The clasp structure of claim 1 wherein said spring means is a flat, U-shaped spring and opposing end portions of said spring define the jaws of the clasp.

4. The lever means of claim 1 wherein the lever is a pivotally mounted lever provided with a cam-like protrusion that serves to force one jaw member into clamping relationship with the other jaw member.

5. The clasp structure of claim 4 wherein an intermediate portion of said spring has an upper surface which continuously contacts the cam-like protrusion of the lever during its rotation for moving the normally elevated upper jaw toward a closed position.

6. The structure of claim 1 further wherein the clasp body is an electrical insulation covering to serve as a housing for the jaws.

7. The structure of claim 1 wherein the upper portion and lower portion of the clasp body have a snap-fit connection therebetween for retaining said portions together when the clasp is assembled.

8. The structure of claim 1 wherein the lower portion has a pair of laterally spaced apart upwardly extending pivot support posts with openings for pivotally supporting the lever means and the clasp includes post-engaging means for preventing lateral deflection of the posts when the clasp is assembled.

9. The clasp of claim 1 wherein the clasp has a housing with an opening therein for receiving a stud of a snap-type biomedical electrode and a retaining means is actuated by the lever when the lever is in an operating mode for forcing the stud to a locked position within the opening.

10. The structure of claim 9 wherein the opening is an oblong opening that is smaller at one end than the other, the stud is adapted to enter a large end of the opening and the retaining means shifts the stud to a locked position within the oblong opening.

11. A biomedical clasp for establishing electrical contact with a patient-contacting electrode comprising, a clasp structure having a front end and a rear end, said clasp structure having a stud receiving opening therein, an operating lever mounted on the clasp structure for movement relative thereto for causing the electrode to be held by the clasp, a movable retaining means supported by the clasp proximate to the stud-receiving opening, the operating lever is operatively associated with the retaining means, the opening in the clasp structure is elongated to permit shifting of a stud longitudinally within the opening and the opening is smaller at one end than the other, and movement of the operating lever to an operative position causes a lower portion of the lever to move toward the smaller end of the opening for exerting a force on the stud to thereby shift the stud in the elongated opening to said smaller portion of the opening for holding the stud within said smaller portion of the opening.

12. The clasp structure of claim 11 wherein the clasp has a housing formed from an insulating material, the retaining means is a portion of a generally U-shaped leaf spring mounted within the housing, said clasp structure has at least one electrically conductive jaw positioned in mating relationship to an opposed cooperating jaw, and the jaws are forced together by movement of the lever to provide a universal clasp that will retain a tab-type electrode between the jaws and will also hold a stud of a snap-type electrode within the opening in the clasp when the lever is moved to a jaw closing position.

13. A biomedical clasp for establishing electrical contact with a patient-contacting electrode comprising, a clasp structure having a front end and a rear end, said clasp structure having a stud receiving opening therein, an operating lever mounted on the clasp structure for movement relative thereto for causing the electrode to be held by the clasp, a movable retaining means supported by the clasp proximate to the stud-receiving opening, the operating lever is operatively associated with the retaining means, movement of the lever to a locking position shifts the retaining means into engagement with a stud thereby locking the stud to the clasp structure, the retaining means is a finger formed from a resilient material supported within the clasp structure in a position to engage a portion of the stud and the lever has an exposed portion for being contacted by a user to deflect the finger in the direction of the stud for shifting the stud to a locked position within the clasp, and the retaining means is a portion of a leaf spring supported by a body portion of the clasp.

14. A universal clasp structure for a biomedical electrode comprising, a clasp body having a jaw-end with a jaw opening for receiving a laterally extending tab of a biomedical electrode, jaws proximate to the jaw-end for engaging the tab and defining said jaw opening, an operating member adapted to be shifted from one position to another for closing the jaws so as to grip the tab of the electrode and establish electrical contact therewith, said clasp body also having a stud-receiving opening therein for receiving a stud of an electrode having an electrically conductive stud that extends upwardly from a surface thereof, a portion of the clasp operating member is operatively positioned for holding said stud in a locked condition in the clasp when said stud is placed within the opening, the clasp has a spring with a stud-retaining finger and the operating member when shifted to an operating position deflects the finger toward the stud for connecting the stud to the clasp, whereby either the jaws or the stud-receiving opening can be employed to receive and make electrical contact with either of two types of biomedical electrodes, namely, an electrode with a laterally extending tab or an electrode having a stud.

15. The clasp structure of claim 14 wherein the finger is intermediate the ends of the spring.

16. A universal clasp structure for establishing electrical connection to a biomedical electrode comprising, a clasp body having a jaw-end, a spring member having a pair of opposed aligned cooperating contact arms to serve as jaws for grasping a tab portion of an electrode placed therebetween, lever means having first and second operating portions, said first operating portion being operatively associated with the spring for forcing the jaw portions of the spring toward one another into locking engagement with the electrode, said spring also having a retaining means positioned to engage and establish electrical connection with a stud of a snap-style electrode, the second operating portion of the lever means is operatively associated with the stud for forcing the retaining means into engagement with the stud to thereby lock the stud to the clasp structure, and said spring is electrically connected to a lead wire to carry electrical signals to or from the clasp structure.

17. The clasp structure of claim 16 wherein the spring is a leaf spring having an opening therein sized to receive the stud and the retaining means engages the stud after the stud has entered the opening for locking the stud within the opening.

18. The clasp structure of claim 17 wherein the opening is elongated and the retaining means comprises a portion of the spring positioned proximate to the stud when the stud is placed within the opening, and the movement of the retaining means engages the stud for holding the stud in a locked condition in the clasp.

19. A universal clasp structure for establishing electrical connection to either a) a tab-style medical electrode with a lateral tab on the edge thereof or b) a snap-style electrode having stud projecting upwardly from a top surface thereof, said clasp structure comprising, a pair of opposed aligned cooperating jaws that move apart or together for grasping a tab portion of an electrode placed therebetween when the jaws are engaged in a closed position for establishing electrical contact with the tab, said clasp structure having a member with an opening therein extending from an outer surface thereof to an inner portion thereof and the opening is sized to receive a stud of a snap-style medical electrode, and an electrical conductor is positioned interiorally of the opening for establishing electrical contact with the stud when the stud is positioned to extend through the opening.

20. The clasp structure of claim 19 wherein the electrical conductor is a sheet of electrically conductive material having a portion thereof aligned inside the opening, and the member is a portion of the clasp structure which is formed from a nonconductor of electricity.

21. A clasp structure for establishing electrical connection to a biomedical electrode comprising, a pair of opposed aligned cooperating jaws that are moveable relative to one another for grasping a tab portion of an electrode placed therebetween when the jaws are in a closed position for establishing electrical contact with the tab of a tab-style medical electrode, the clasp structure includes a metal sheet, and said metal sheet has
a) an electrically conductive first portion for establishing electrical contact with the tab of said tab-style electrode and
b) said metal sheet has a second portion for establishing electrical contact with a stud of a snap-style electrode, the clasp structure includes a means for holding the stud in a position for establishing electrical contact with said second portion of the metal sheet, said clasp structure has a body formed from an insulating material and the second portion of the metal sheet is located interiorally of an opening within the clasp structure and is positioned proximate the opening for contacting the stud when the stud extends through the opening into the clasp, and the opening is elongated for enabling the stud to be introduced into the clasp structure and then shifted in the opening to a locked position within the opening.

22. The clasp of claim 21 wherein the clasp structure includes upper and lower connected clasp members each formed from plastic resin and the opening is in one of the clasp members.

* * * * *